United States Patent
Kishi et al.

(10) Patent No.: US 10,085,813 B2
(45) Date of Patent: Oct. 2, 2018

(54) MANIPULATOR AND MANIPULATOR SYSTEM

(71) Applicant: OLYMPUS CORPORATION, Tokyo (JP)

(72) Inventors: Kosuke Kishi, Tokyo (JP); Shingo Nakayama, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 321 days.

(21) Appl. No.: 15/002,515

(22) Filed: Jan. 21, 2016

(65) Prior Publication Data

US 2016/0135913 A1 May 19, 2016

Related U.S. Application Data

(63) Continuation of application No. PCT/JP2014/067498, filed on Jul. 1, 2014.

(30) Foreign Application Priority Data

Jul. 25, 2013 (JP) ................................ 2013-154468

(51) Int. Cl.
*A61B 34/00* (2016.01)
*A61B 1/008* (2006.01)
*A61B 1/005* (2006.01)

(52) U.S. Cl.
CPC .............. *A61B 34/72* (2016.02); *A61B 1/008* (2013.01); *A61B 1/0055* (2013.01)

(58) Field of Classification Search
CPC ............................ A61B 1/0055; A61B 1/0056
See application file for complete search history.

(56) References Cited

U.S. PATENT DOCUMENTS

2004/0249367 A1 12/2004 Saadat et al.
2006/0041188 A1* 2/2006 Dirusso ................ A61B 1/0055
  600/146

(Continued)

FOREIGN PATENT DOCUMENTS

CN    101610709 A    12/2009
JP    H05-199982 A    8/1993

(Continued)

OTHER PUBLICATIONS

International Search Report dated Sep. 2, 2014 issued in PCT/JP2014/067498.

(Continued)

*Primary Examiner* — Terence Boes
(74) *Attorney, Agent, or Firm* — Scully, Scott, Murphy & Presser, P.C.

(57) ABSTRACT

Provided is a manipulator including a distal-end joint group and a proximal-end joint group that are arranged adjacent to each other in a distal-end section of an insertion part in a longitudinal axis direction and that are configured to bend the distal-end section. The proximal-end joint group includes a plurality of proximal-end bending joints bendable about axes that are lined-up side-by-side to bend the distal-end section through 180° or more. The distal-end joint group includes first distal-end bending joints disposed on a distal side of the proximal-end joint group and bendable about axes crossing a plane including the axes of the proximal-end bending joints and the longitudinal axis; and a second distal-end bending joint disposed in the longitudinal axis direction relative to the axes of the first distal-end bending joints and bendable about an axis that is lined-up side-by-side with the axes of the proximal-end bending joints.

6 Claims, 15 Drawing Sheets

(56) References Cited

U.S. PATENT DOCUMENTS

| | | | |
|---|---|---|---|
| 2006/0178560 A1 | 8/2006 | Saadat et al. | |
| 2008/0208001 A1* | 8/2008 | Hadani | A61B 1/00071 600/128 |
| 2009/0248202 A1* | 10/2009 | Osuka | A61B 1/0055 700/245 |
| 2010/0292558 A1* | 11/2010 | Saadat | A61B 1/00085 600/407 |
| 2011/0071508 A1 | 3/2011 | Duval et al. | |
| 2014/0088361 A1* | 3/2014 | Hrayr | A61B 1/00183 600/111 |
| 2016/0316996 A1* | 11/2016 | Nakayama | A61B 1/0055 |

FOREIGN PATENT DOCUMENTS

| | | |
|---|---|---|
| JP | H06-217929 A | 8/1994 |
| JP | 2005-137701 A | 6/2005 |
| JP | 2007-054400 A | 3/2007 |
| JP | 2008-048788 A | 3/2008 |
| JP | 2009-539573 A | 11/2009 |
| JP | 2011-118924 A | 6/2011 |
| JP | 2012-196269 A | 10/2012 |
| JP | 5197980 B | 5/2013 |
| WO | 2005/086945 A2 | 9/2005 |
| WO | 2007/146987 A2 | 12/2007 |
| WO | 2012/014532 A1 | 2/2012 |

OTHER PUBLICATIONS

Extended Supplementary European Search Report dated Mar. 7, 2017 in European Patent Application No. 14 82 9651.0.

* cited by examiner

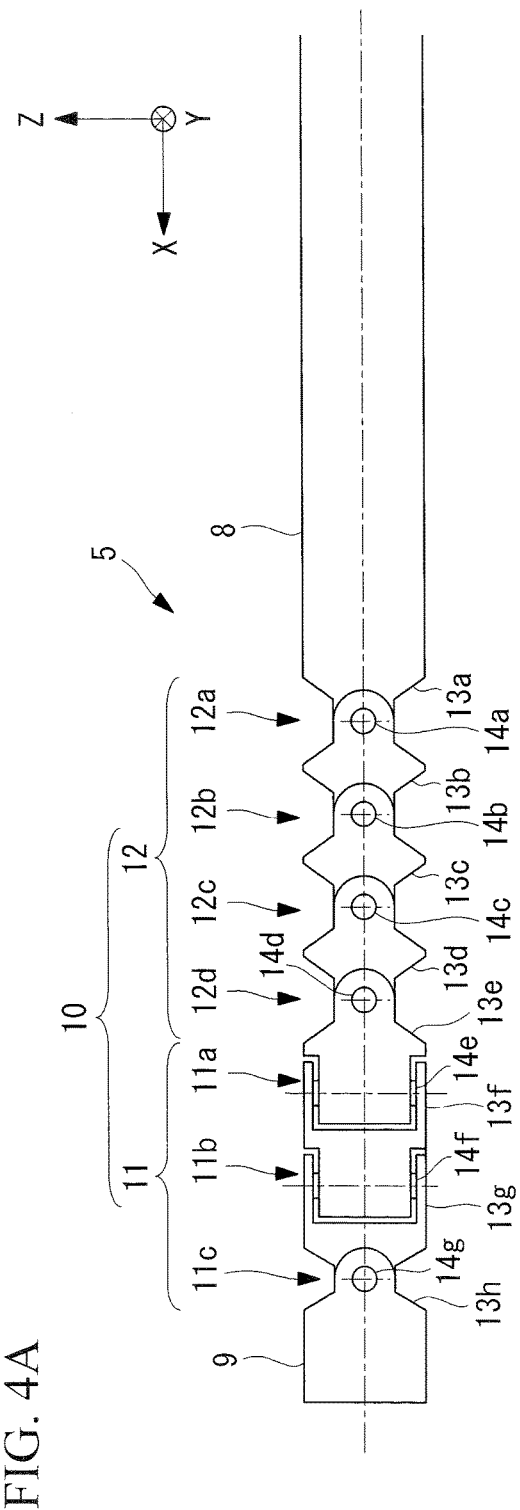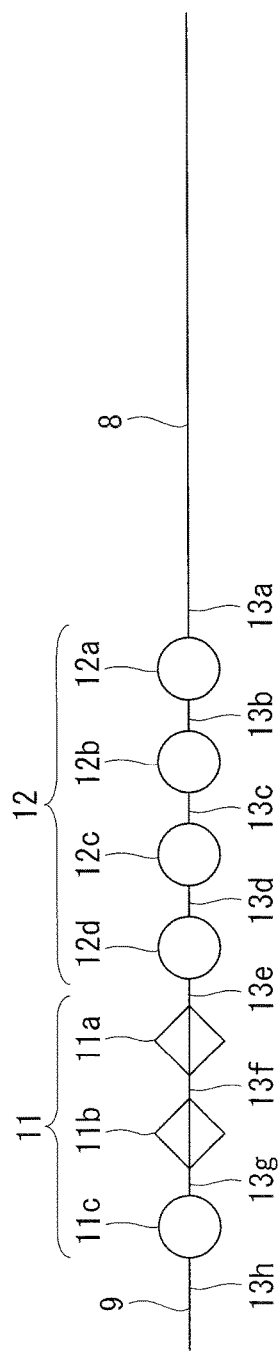

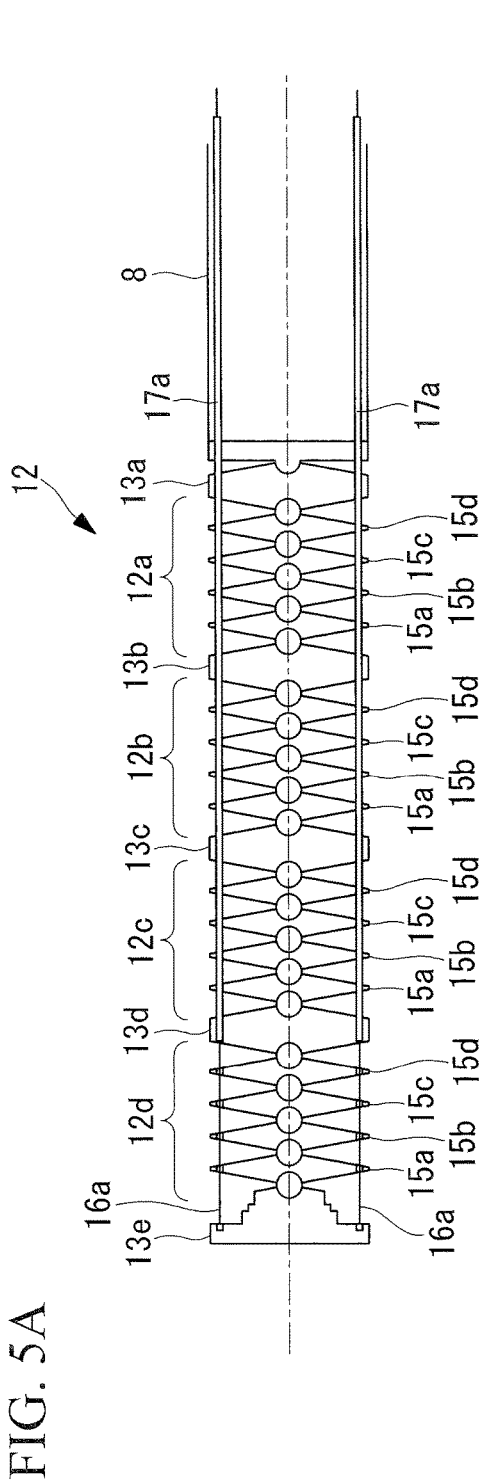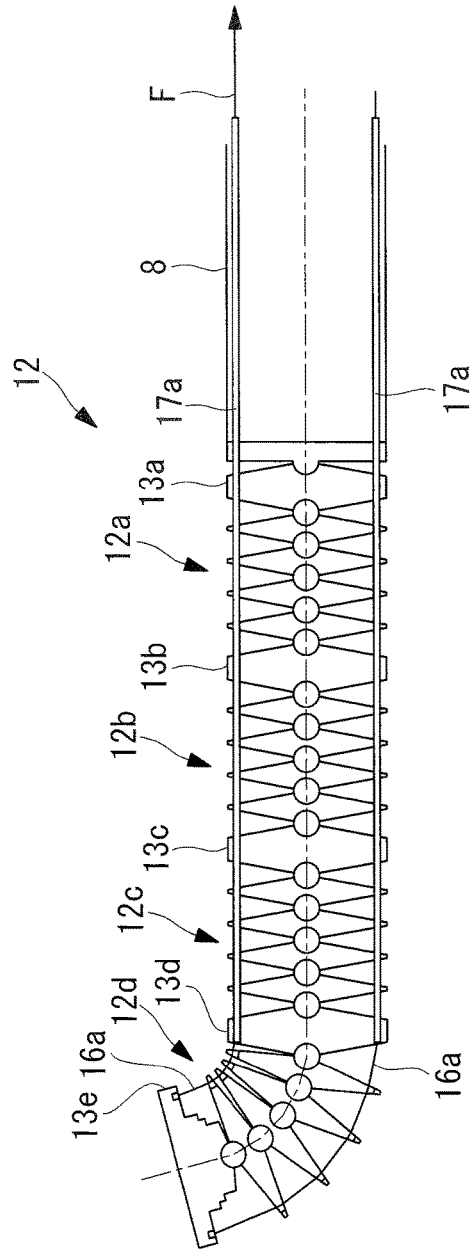
FIG. 5A
FIG. 5B

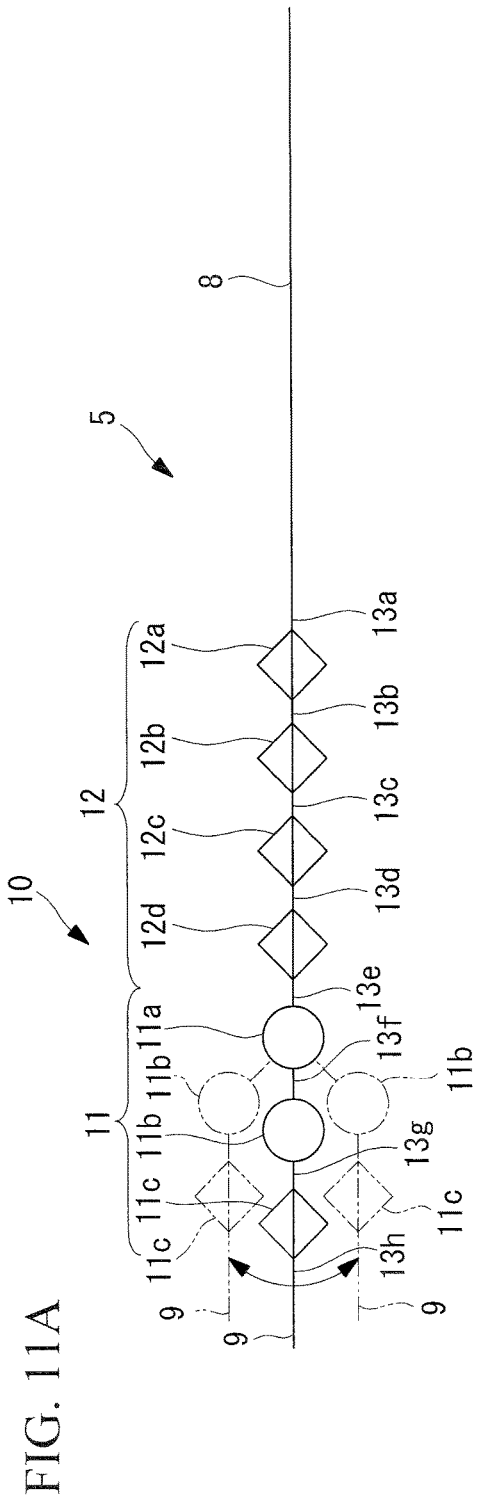
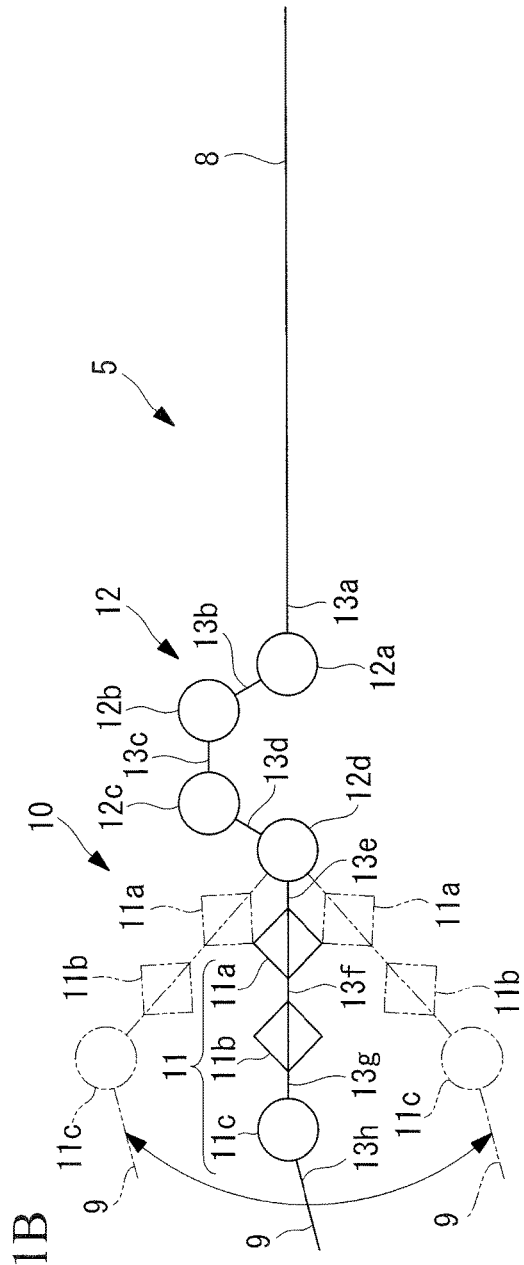
FIG. 11A
FIG. 11B

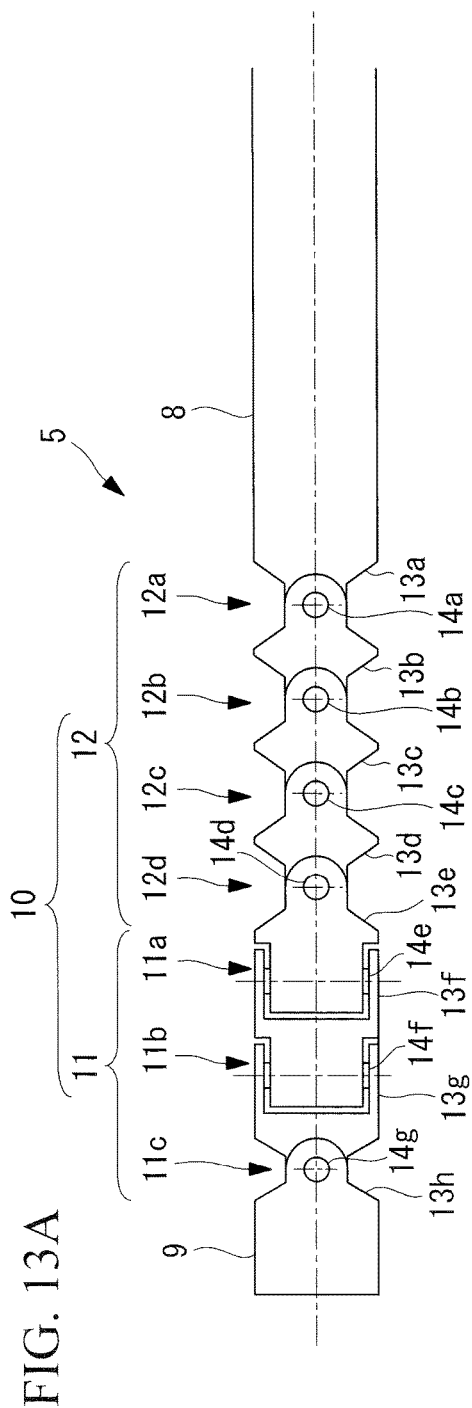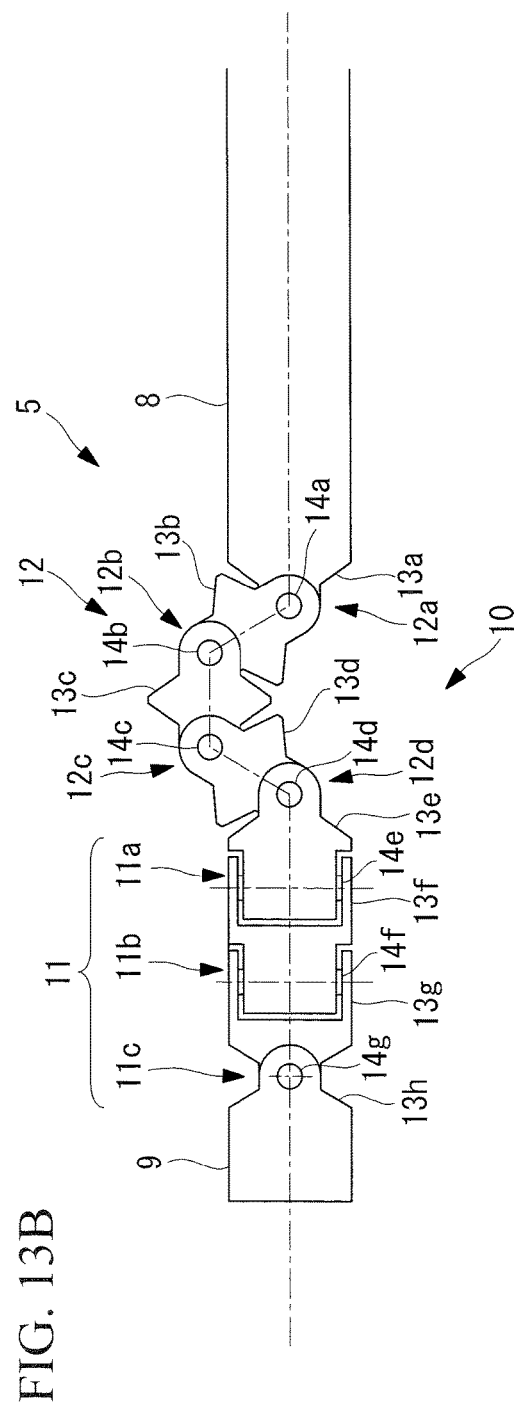

MANIPULATOR AND MANIPULATOR SYSTEM

CROSS-REFERENCE TO RELATED APPLICATIONS

This is a continuation of International Application PCT/JP2014/067498, with an international filing date of Jul. 1, 2014, which is hereby incorporated by reference herein in its entirety. This application claims the benefit of Japanese Patent Application No. 2013-154468, the content of which is incorporated herein by reference.

TECHNICAL FIELD

The present invention relates to manipulators and manipulator systems.

BACKGROUND ART

There is a known endoscope including two bending sections disposed at the distal end of an insertion part and adjacent to each other in the longitudinal direction (see, for example, patent literature PTL 1 below). This endoscope allows the observation and treatment of an affected area located toward the front in the insertion direction. Also known is an endoscope having a U-shaped bend at the distal end of an insertion part (see, for example, patent literature PTL 2 below).

However, when used for treatment in the lumen of an organ such as the large intestine, the above endoscopes in PTLs 1 and 2 present a problem in that an affected area located in front of, behind, or across a fold on the inner wall of the lumen in the insertion direction cannot be sufficiently treated.

CITATION LIST

Patent Literature

{PTL 1}
Japanese Unexamined Patent Application, Publication No. 2012-196269
{PTL 2}
Japanese Translation of PCT International Application, Publication No. 2009-539573

SUMMARY OF INVENTION

Solution to Problem

The present invention provides the following solutions.

An aspect of the present invention provides a manipulator including a distal-end joint group and a proximal-end joint group that are arranged adjacent to each other in a distal-end section of an elongated insertion part in a longitudinal axis direction and that are configured to bend the distal-end section. The proximal-end joint group includes a plurality of proximal-end bending joints bendable about axes that are lined-up side-by-side to bend the distal-end section through 180° or more. The distal-end joint group includes a first distal-end bending joint disposed on a distal side of the proximal-end joint group and bendable about an axis crossing a plane including the axes of the proximal-end bending joints and the longitudinal axis; and a second distal-end bending joint disposed in the longitudinal axis direction relative to the axis of the first distal-end bending joint and bendable about an axis that is lined-up side-by-side with the axes of the proximal-end bending joints.

FIG. 4A is a simplified side view of the bending section in FIG. 3.

FIG. 4B is a schematic side view of the bending section in FIG. 3.

FIG. 5A is a side view showing the state where the proximal-end joint group is straight and shows a proximal-end joint group of the bending section in FIG. 3.

FIG. 5B is a side view showing the state where the most distal joint is bent and shows a proximal-end joint group of the bending section in FIG. 3.

FIG. 11A is a schematic plan view illustrating the translation of the tip of the endoscope in FIG. 2 by the bending section.

FIG. 11B is a schematic side view illustrating the translation of the tip of the endoscope in FIG. 2 by the bending section.

FIG. 13A is a side view showing the state where the bending section is straight and illustrates how the bending section of the endoscope in FIG. 2 is advanced and retracted like an inchworm.

FIG. 13B is a side view showing the state where the proximal-end joint group is contracted and illustrates how the bending section of the endoscope in FIG. 2 is advanced and retracted like an inchworm.

DESCRIPTION OF EMBODIMENTS

A manipulator and manipulator system according to an embodiment of the present invention will be described below with reference to the drawings.

Figure 1:
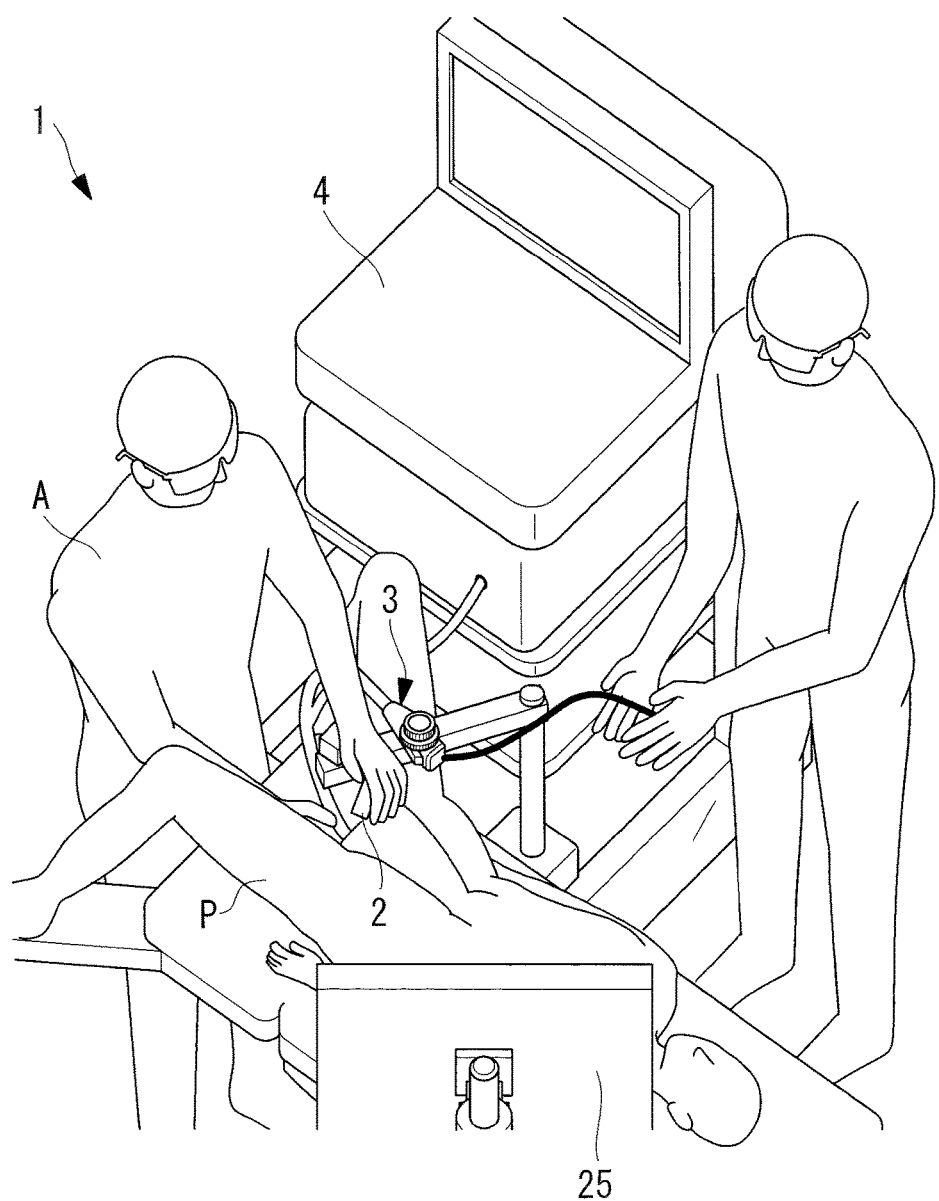
FIG. 1 is an overall view showing an endoscope system including an endoscope according to an embodiment of the present invention.

As shown in FIG. 1, the manipulator system according to this embodiment is an endoscope system 1 including a master device 2 that is manipulated by a doctor (operator) A, a slave device 3 that is driven by inputs via the master device 2, a controller 4 that controls the slave device 3 based on the inputs to the master device 2, and a monitor 25.

Figure 2:
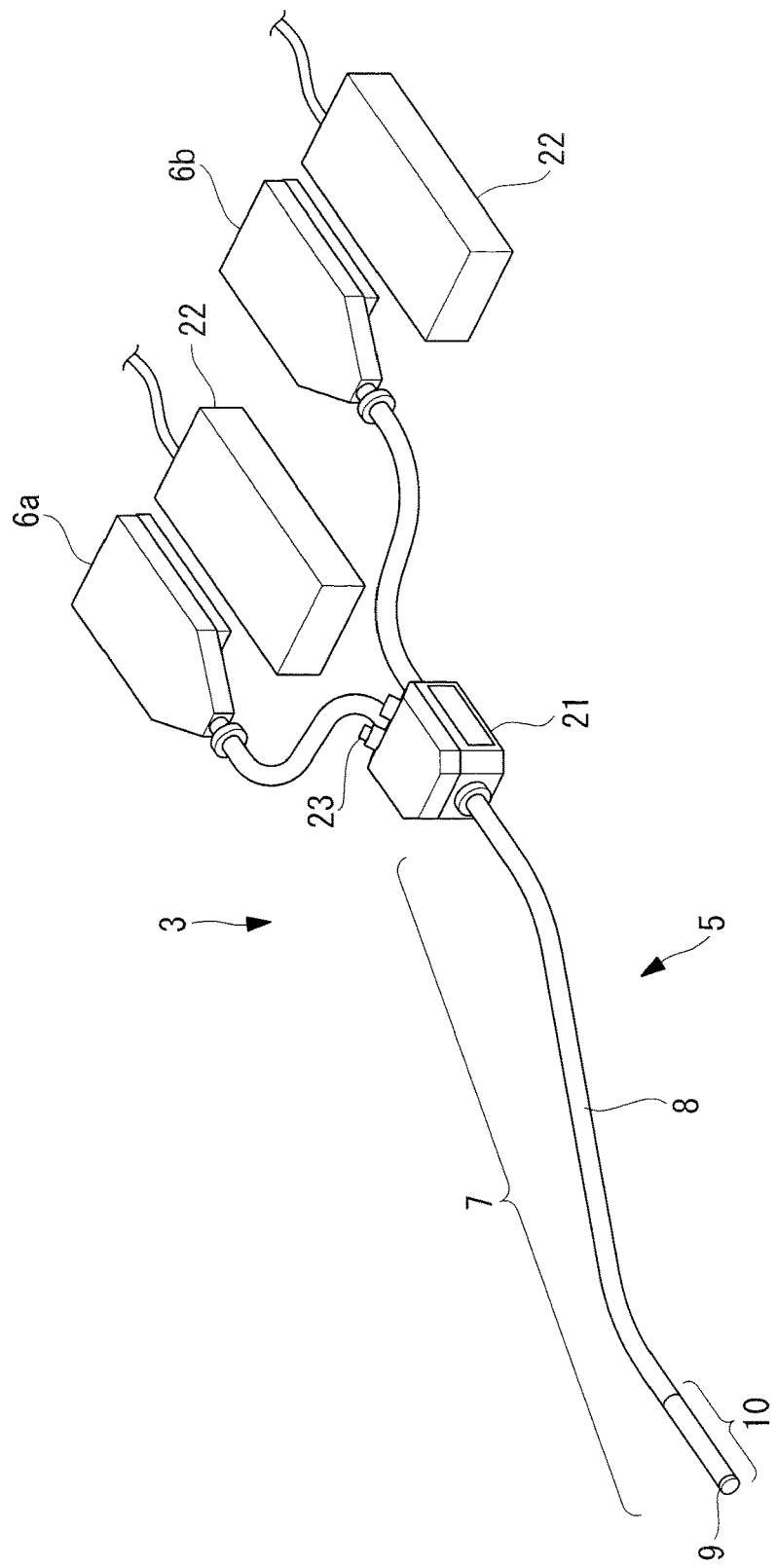
FIG. 2 is a perspective view showing a slave device including the endoscope.

As shown in FIG. 2, the slave device 3 includes an endoscope 5 according to this embodiment for insertion into the lumen of a patient P and drive units 6a and 6b that drive the endoscope 5.

The manipulator according to this embodiment is the endoscope 5, which is a flexible endoscope including a bendable flexible elongated insertion part 7 that has an elongated flexible section 8, a tip 9 disposed at the distal end thereof, and a bending section 10 disposed between the tip 9 and the flexible section 8. Although the endoscope 5 according to this embodiment is a flexible endoscope, it may instead be a rigid endoscope including an elongated rigid section.

Figure 3:
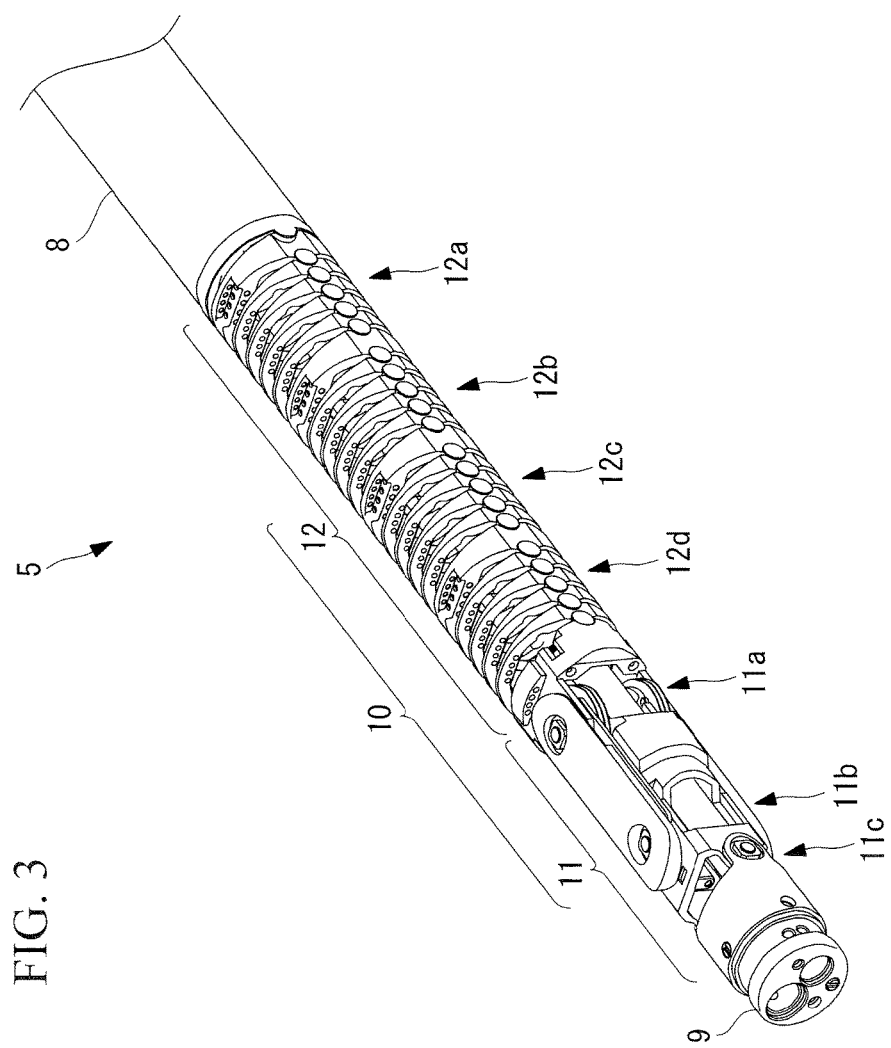
FIG. 3 is a partial perspective view showing a bending section of the endoscope in FIG. 2.

As shown in FIG. 3, the bending section 10 includes a distal-end joint group 11 and a proximal-end joint group 12 for changing the position and orientation of the tip 9 relative to the distal end of the flexible section 8. The distal-end joint group 11 and the proximal-end joint group 12 are arranged in line in the longitudinal direction of the insertion part 7. FIG. 4A is a simplified view of the bending section 10, and FIG. 4B is a schematic view of the bending section 10.

The proximal-end joint group 12 includes a plurality of bending joints, for example, four bending joints (proximal-end bending joints) 12a to 12d. Each of the bending joints 12a to 12d is disposed between two of link members 13a to 13e such that the relative angle between any two of the link members 13a to 13e is variable.

The bending joints 12a to 12d are independently bendable about axes 14a to 14d, respectively, arranged parallel to each other (i.e., in the Y-axis direction) at intervals in the longitudinal direction of the insertion part 7, i.e., in the longitudinal axis direction of the link members 13a to 13e. For example, the bending joints 12a to 12d are configured to be bendable over a bending angle range of ±60° so that the entire proximal-end joint group 12 is bendable through ±240°. The axes 14a to 14d do not necessarily have to extend parallel to each other, but may lined-up side-by-side in a manner that allows bending.

For example, as shown in FIGS. 5A, 5B, 6A and 6B, each of the bending joints 12a to 12d includes a plurality of pieces, for example, four pieces 15a to 15d, joined together so as to be pivotable relative to each other between two of the link members 13a to 13e, and ends of wires 16a extending through through-holes provided at ends of the pieces 15a to 15d are fixed to the most distal link member 13e.

FIGS. 5A and 5B illustrate the motion of the most distal bending joint 12d of the proximal-end joint group 12. Two wires 16a are guided by two sheathes 17a extending in the longitudinal direction from the proximal end of the insertion part 7 to the link member 13d at the proximal end of the bending joint 12d and are fixed to the link member 13e at the distal end of the bending joint 12d. By applying a tension F to one of the wires 16a, the most distal bending joint 12d, which is initially straight, as shown in FIG. 5A, can be bent alone in one direction, as shown in FIG. 5B.

Figure 6A:
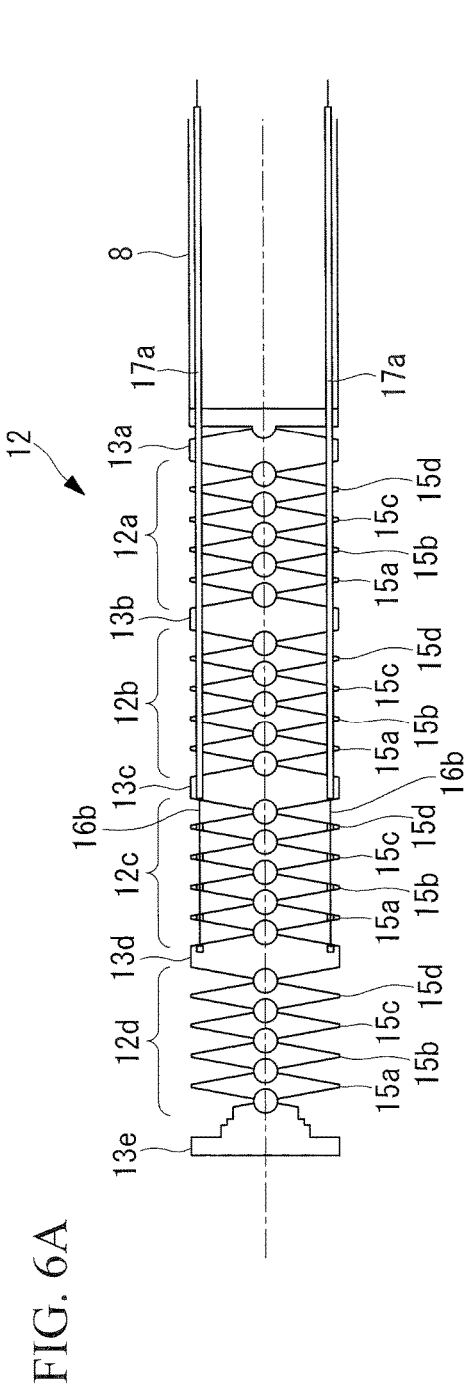
FIG. 6A is a side view showing the state where the proximal-end joint group is straight and shows the proximal-end joint group of the bending section in FIG. 3.
Figure 6B:
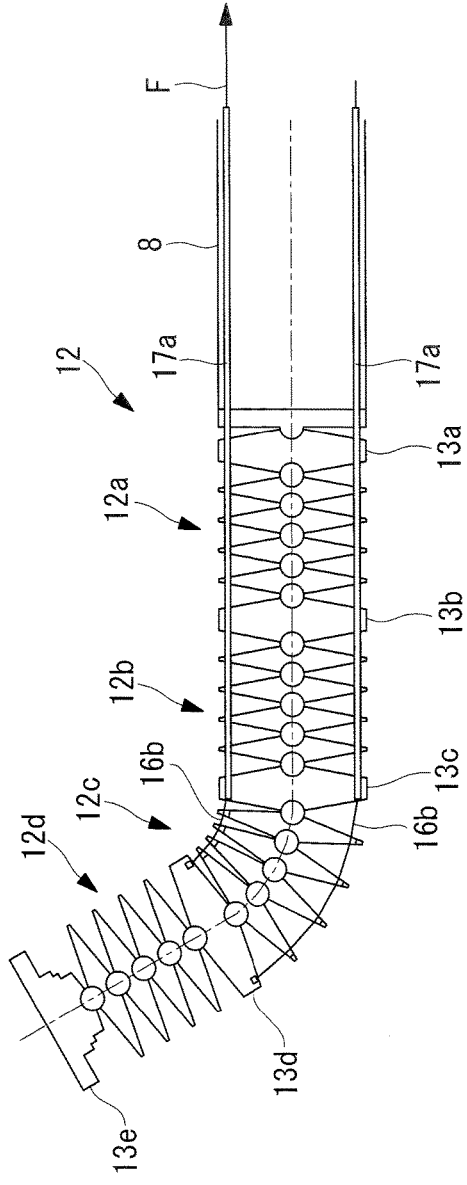
FIG. 6B is a side view showing the state where the second-most distal joint is bent and shows the proximal-end joint group of the bending section in FIG. 3.

FIGS. 6A and 6B illustrates the motion of the second-most distal bending joint 12c of the proximal-end joint group 12. Two wires 16b are guided by two sheathes 17a extending in the longitudinal direction from the proximal end of the insertion part 7 to the link member 13c at the proximal end of the bending joint 12c and are fixed to the link member 13d at the distal end of the bending joint 12c. By applying a tension to one of the wires 16b, the second-most distal bending joint 12c, which is initially straight, as shown in FIG. 6A, can be bent alone in one direction, as shown in FIG. 6B.

Although not illustrated, the third- and fourth-most distal bending joints 12b and 12a are configured in the same manner.

The distal-end joint group 11 includes a plurality of bending joints, for example, three bending joints (distal-end bending joints) 11a to 11c. Each of the bending joints 11a to 11c is disposed between two of link members 13e to 13h such that the relative angle between any two of the link members 13e to 13h is variable.

As shown in FIGS. 4A and 4B, the two proximal bending joints 11a and 11b are configured such that the link members 13f to 13h are pivotable about axes 14e and 14f, respectively, extending perpendicular to a plane including the axis 14d of the most distal bending joint 12d of the proximal-end joint group 12 and the longitudinal axis of the link members 13e to 13h (i.e., extending in the Z-axis direction). The most distal bending joint 11c is configured such that the tip 9 is pivotable about an axis 14g extending perpendicular to a plane including the axes 14e and 14f of the bending joints 11a and 11b and the longitudinal axis of the link members 13e to 13h (i.e., extending in the Y-axis direction). The axes 14e and 14f do not necessarily have to extend perpendicular to the plane including the axis 14d and the longitudinal axis, but may cross the plane in any manner that allows bending.

Figure 7A:
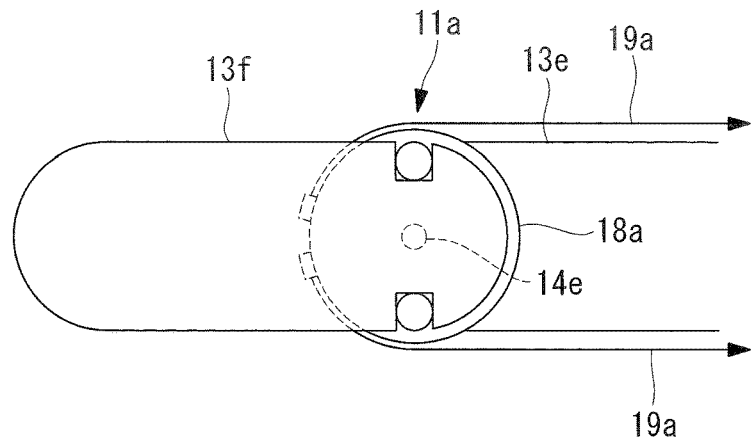
FIG. 7A is a side view showing the state where the bending joint is straight and shows the most proximal bending joint of the distal-end joint group of the bending section in FIG. 3.
Figure 7B:
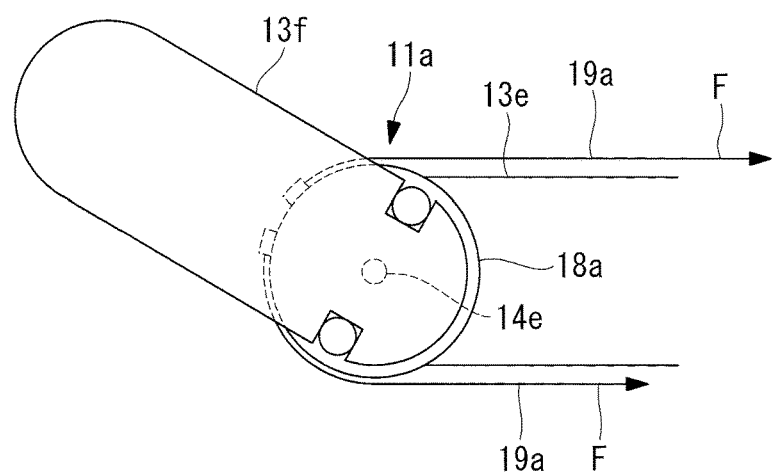
FIG. 7B is a side view showing the state where the bending joint is bent in one direction and shows the most proximal bending joint of the distal-end joint group of the bending section in FIG. 3.
Figure 7C:
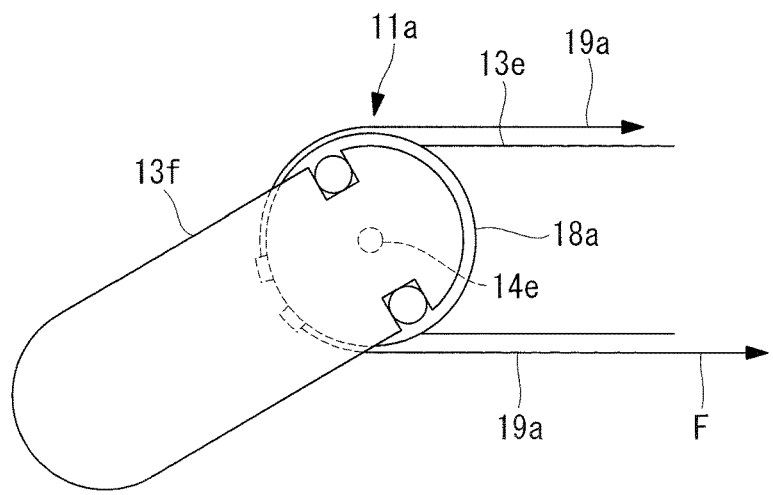
FIG. 7C is a side view where the bending joint is bent in another direction and shows the most proximal bending joint of the distal-end joint group of the bending section in FIG. 3.

As shown in FIGS. 7A, 7B and 7C, the most proximal bending joint 11a of the distal-end joint group 11 is configured such that the distal link member 13f is pivotable relative to the proximal link member 13e, for example, by applying a tension F to wires 19a fixed at the ends thereof to a pulley 18a fixed to the link member 13f and pivotably coupled to the link member 13e. There are two wires 19a fixed at the ends thereof to the pulley 18a such that the pulley 18a is rotatable in opposite directions by the tension F.

Figure 8A:
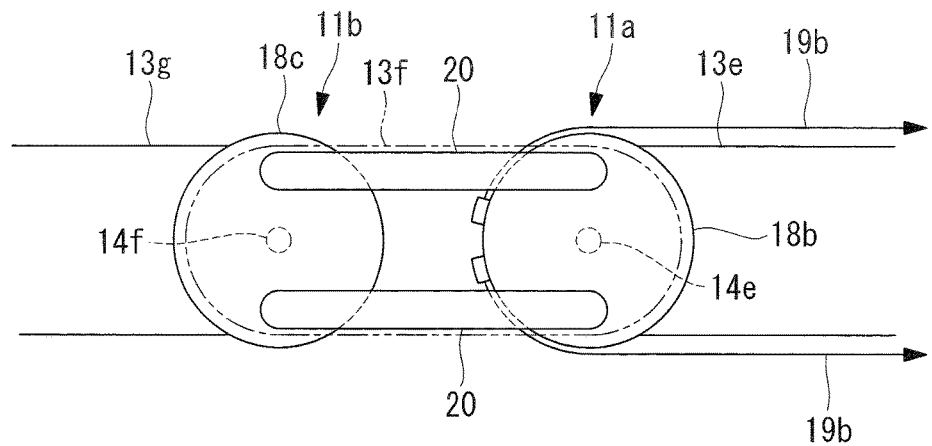
FIG. 8A is a side view showing the state where the bending joint is straight and shows the second-most proximal bending joint of the distal-end joint group of the bending section in FIG. 3.
Figure 8B:
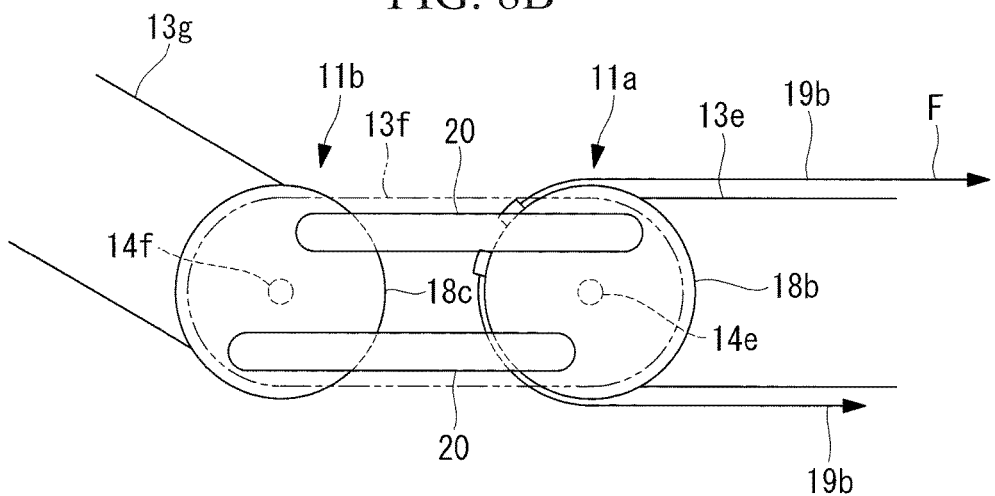
FIG. 8B is a side view showing the state where the bending joint is bent in one direction and shows the second-most proximal bending joint of the distal-end joint group of the bending section in FIG. 3.
Figure 8C:
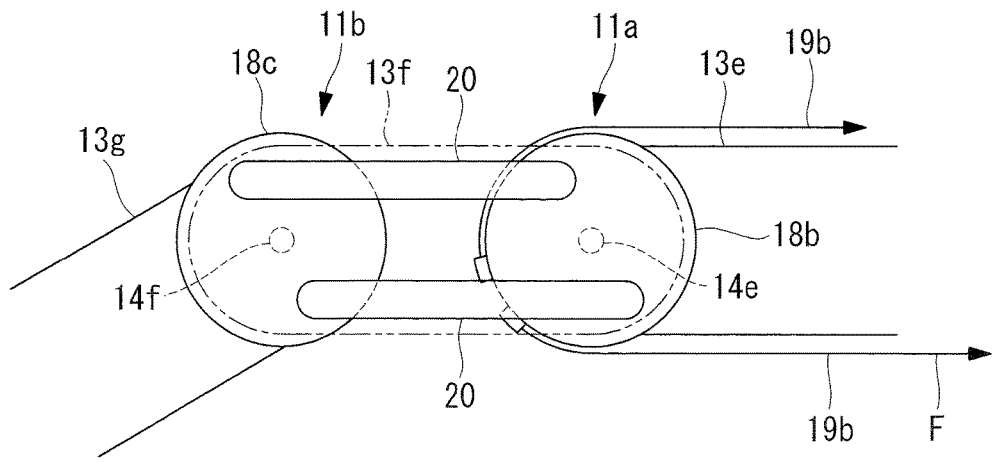
FIG. 8C is a side view where the bending joint is bent in another direction and shows the second-most proximal bending joint of the distal-end joint group of the bending section in FIG. 3.

As shown in FIGS. 8A, 8B and 8C, the second-most proximal bending joint 11b of the distal-end joint group 11 includes a proximal-end pulley 18b pivotably coupled to the two link members 13e and 13f, a distal-end pulley 18c fixed to the distal link member 13g and pivotably coupled to the proximal link member 13f, and coupling links 20 coupling the two pulleys 18b and 18c. The link member 13g is pivotable relative to the link member 13f by applying a tension F to wires 19b fixed at the ends thereof to the proximal-end pulley 18b. There are two wires 19b fixed at the ends thereof to the proximal-end pulley 18b such that the proximal-end pulley 18b is rotatable in opposite directions by the tension F.

Figure 9A:
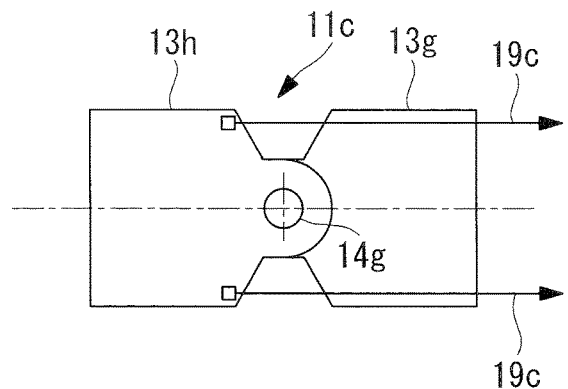
FIG. 9A is a side view showing the state where the bending joint is straight and shows the most distal bending joint of the distal-end joint group of the bending section in FIG. 3.
Figure 9B:
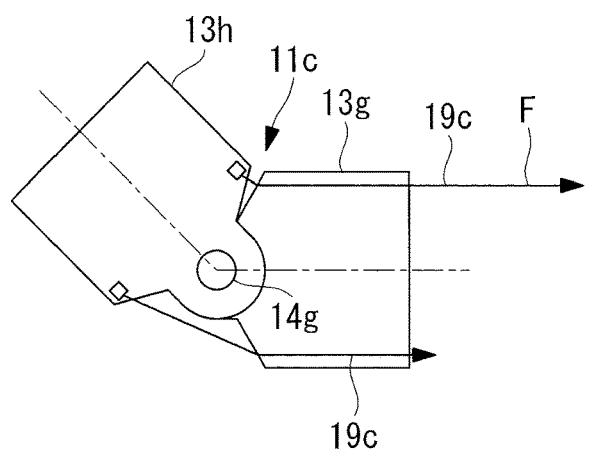
FIG. 9B is a side view showing the state where the bending joint is bent in one direction and shows the most distal bending joint of the distal-end joint group of the bending section in FIG. 3.
Figure 9C:
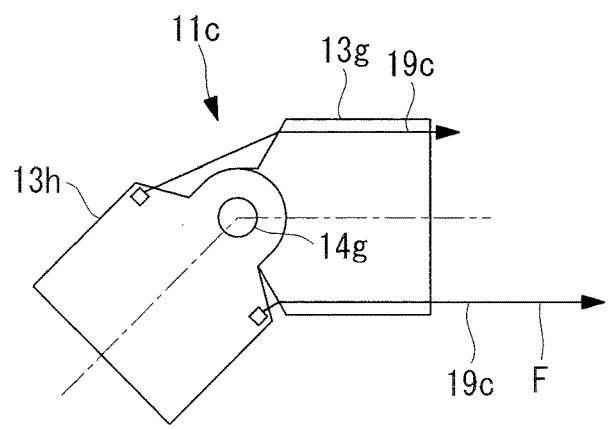
FIG. 9C is a side view where the bending joint is bent in another direction and shows the most distal bending joint of the distal-end joint group of the bending section in FIG. 3.

As shown in FIGS. 9A, 9B and 9C, the most distal bending joint 11c of the insertion part 7 is configured such that the two link members 13g and 13h are coupled together so as to be pivotable about the axis 14g relative to each other and the link member 13h is pivotable relative to the link member 13g by applying a tension F to wires 19c fixed at the ends thereof to the distal link member 13h.

All of the wires 16a, 16b, and 19a to 19c for moving the bending joints 11a to 11c and 12a to 12d extend through the flexible section 8 toward the proximal end of the flexible section 8.

As shown in FIG. 2, the drive units 6a and 6b include a distal-end drive unit 6a that drives the distal-end joint group 11 and a proximal-end drive unit 6b that drives the proximal-end joint group 12. Each of the drive units 6a and 6b is connected to the flexible section 8 of the endoscope 5 via a relay 21. The drive units 6a and 6b include sliders (not shown) attached to the proximal ends of the wires 16a, 16b, and 19a to 19c extending through the flexible section 8 toward the proximal end so that the proximal ends of the wires 16a, 16b, and 19a to 19c can be pulled to adjust the force F separately applied to each of the wires 16a, 16b, and 19a to 19c. Each drive unit is attachable to and detachable from a drive source 22 including an electric actuator, or a manually operated master for manual operation (not shown).

The actuators for the drive sources 22 are, for example, linear actuators such as linear motors. When the drive units 6a and 6b are attached to the actuators, the actuators engage with the sliders of the drive units 6a and 6b, and the sliders are slid by the operation of the actuators to apply the tension F to the wires 16a, 16b, and 19a to 19c.

When the drive units 6a and 6b are attached to manually operated masters, the manipulating parts thereof engage with the sliders of the drive units 6a and 6b, and the sliders are slid by a force applied by the doctor A to apply a tension F to the wires 16a, 16b, and 19a to 19c.

The relay 21 has a port 23 through which a surgical instrument is inserted into a forceps channel (not shown) extending in the longitudinal direction of the insertion part 7 to the distal-end surface thereof.

As shown in FIG. 1, the master device 2 is an input device having the same number of joints as the bending section 10 of the endoscope 5 and being geometrically similar thereto. The individual joints have detectors (not shown), such as encoders, that detect the bending angles thereof. When the doctor A grasps and moves the end of the master device 2, the detectors detect the bending angles of the joints of the master device 2 and output bending angle signals.

The controller 4 controls the drive units 6a and 6b so that the bending angles of the bending joints 11a to 11c and 12a to 12d of the bending section 10 of the endoscope 5 are identical to the bending angles of the joints of the master device 2 indicated by the bending angle signals output from the master device 2.

The operation of the thus-configured endoscope 5 and endoscope system 1 according to this exemplary embodiment will be described below.

For observation and treatment in the lumen of the patient P using the endoscope 5 according to this embodiment, a manually operated master is attached only to the distal-end drive unit 6a that drives the distal-end joint group 11 before the insertion of the endoscope 5 into the lumen.

The doctor A holds the insertion part 7 with his or her right hand and inserts the endoscope 5 into the lumen in the same way as he or she does with a conventional endoscope while manipulating the manually operated master with his or her left hand. During this procedure, an image of the interior of the lumen is captured and displayed on the monitor 25 by operating the endoscope 5. The doctor A manipulates the manually operated master to drive the distal-end joint group 11 while watching the monitor 25 and advances the insertion part 7 through the lumen until the tip 9 of the endoscope 5 approaches the affected area.

In this state, no drive source 22 or manually operated master is attached to the proximal-end drive unit 6b that drives the proximal-end joint group 12; therefore, the proximal-end joint group 12 moves passively in unison with the motion of the distal-end joint group 11. This prevents the proximal-end joint group 12 from interfering with the insertion motion.

When the tip 9 of the insertion part 7 approaches the affected area, the manually operated master is replaced with a drive source 22, another drive source 22 is attached to the proximal-end drive unit 6b, and the doctor A manipulates the master device 2.

Figure 10:
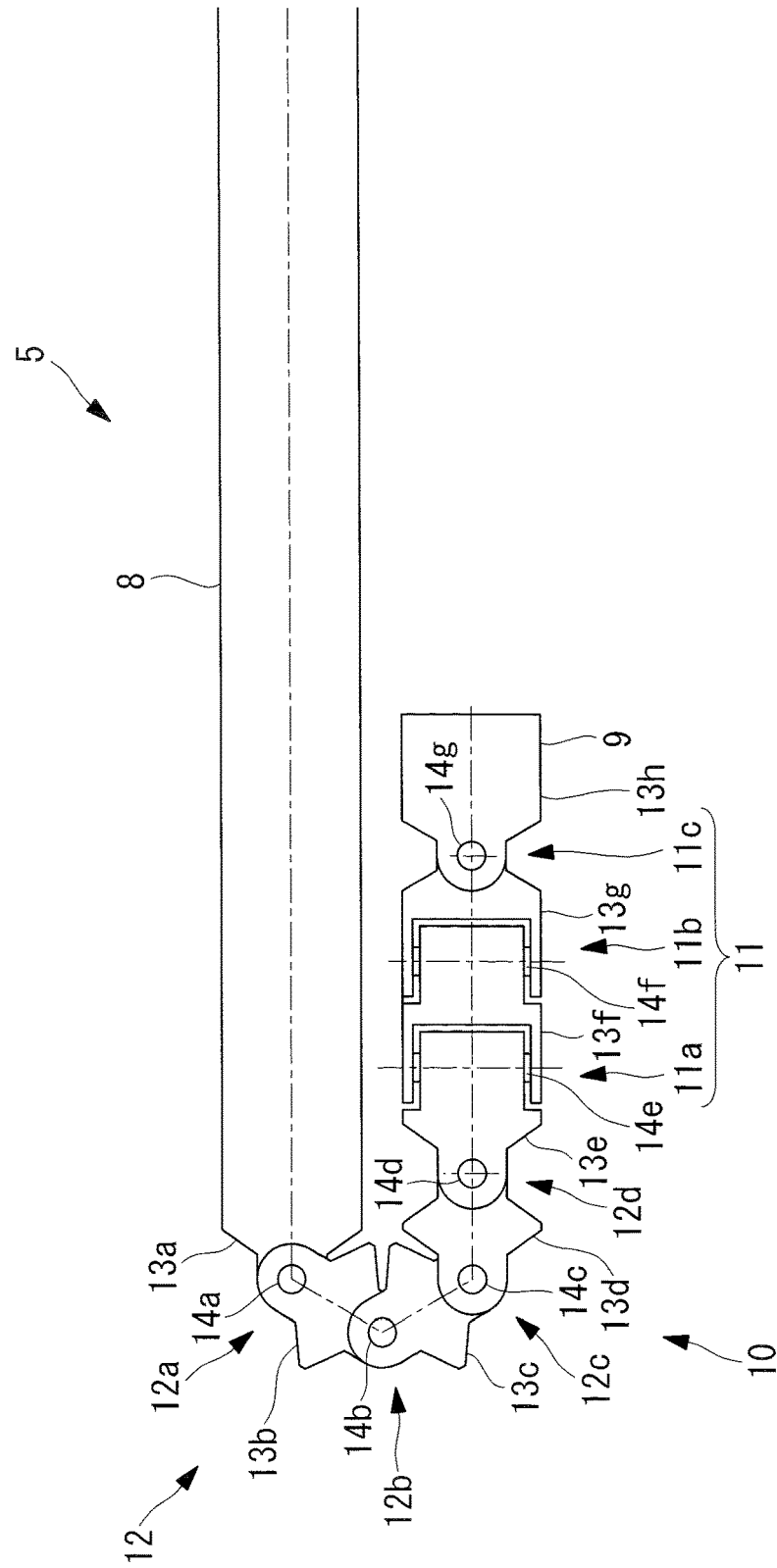
FIG. 10 is a simplified side view showing the state where the bending section of the endoscope in FIG. 2 is bent through 180° by the proximal-end joint group of the bending section.

Since the proximal-end joint group 12 of the endoscope 5 according to this embodiment includes the four bending joints 12a to 12d, which bend through a total of ±240°, the bending section 10 can be bent into a U-shape to direct the distal-end surface of the endoscope 5 toward the back, as shown in FIG. 10. After the bending section 10 is bent into a U-shape, there is a margin in the moving range of the bending joints 12a to 12d; therefore, the tip 9 of the insertion part 7 can be advanced and retracted. This is advantageous in that the distal-end surface of the insertion part 7 can be directed to a position suitable for observation or treatment even if the affected area is located toward the back in the insertion direction, for example, behind a fold in the lumen, rather than toward the front in the insertion direction.

The distal end of the insertion part 7 of the endoscope 5 according to this embodiment can be turned through 180° only by the motion of the proximal-end joint group 12. After the distal end of the insertion part 7 is turned through 180°, the distal-end surface of the insertion part 7 can be moved to any position three-dimensionally by the three bending joints 11a to 11c of the distal-end joint group 11. As shown in FIG. 11A, the endoscope 5 according to this embodiment allows the tip 9 to be translated in a direction perpendicular to the bending direction of the proximal-end joint group 12 by the cooperative motion of the two bending joints 11a and 11b that form the distal-end joint group 11. As shown in FIG. 11B, the endoscope 5 according to this embodiment also allows the tip 9 to be translated in the bending direction of the proximal-end joint group 12 by the cooperative motion of the most distal bending joint 12d of the proximal-end joint group 12 and the most distal bending joint 11c of the proximal-end joint group 11.

That is, the tip 9 can be translated while being maintained in the same orientation by setting the orientation of the tip 9 in two orthogonal directions using the two distal bending joints 11b and 11c of the distal-end joint group 11 and canceling the pivoting of the tip 9 due to the two distal bending joints 11b and 11c by the cooperative motion of the two proximal bending joints 11a and 12d. This allows observation and treatment with reduced interference between the tip 9 and the inner wall of the lumen.

Figure 12:
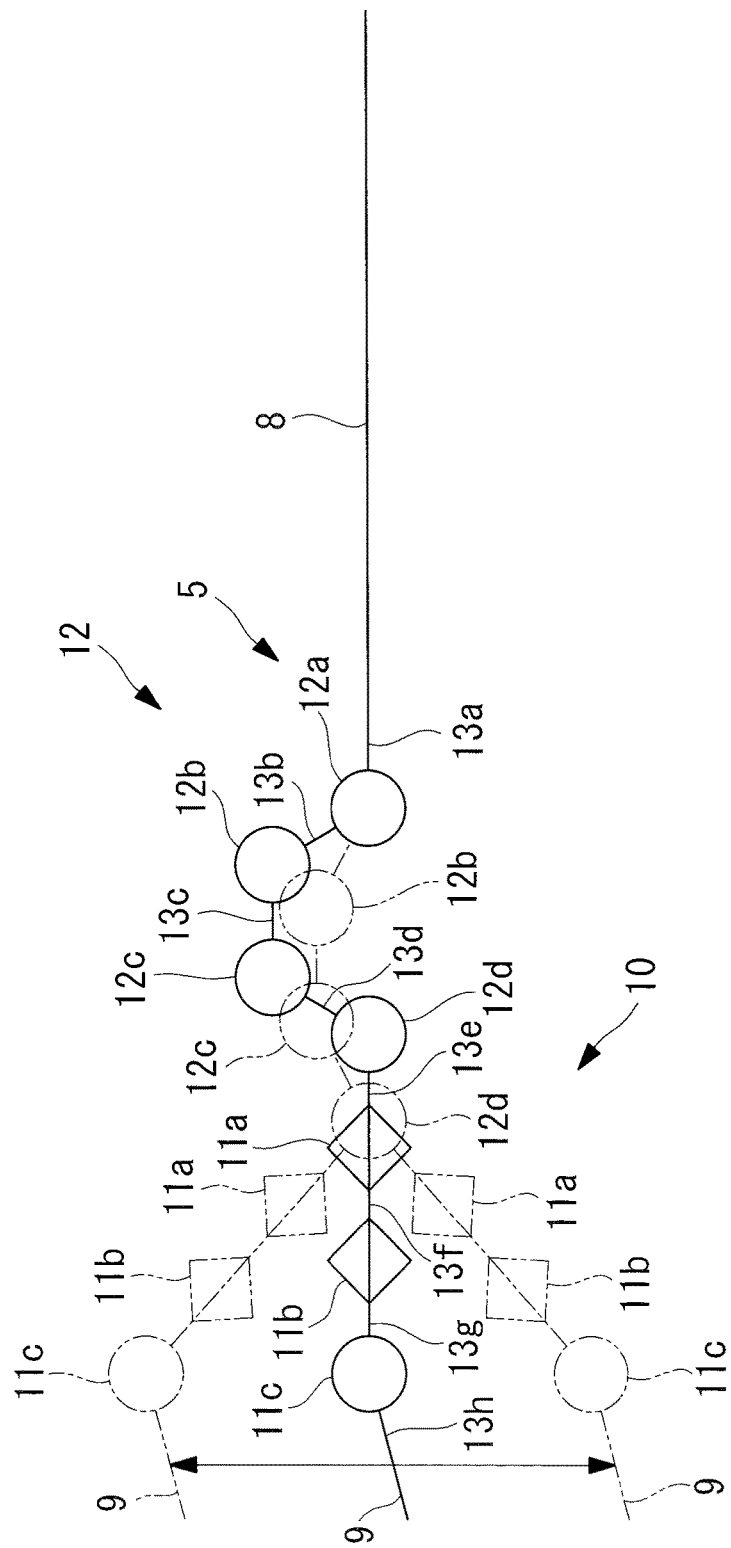
FIG. 12 is a schematic side view illustrating the linear translation of the tip of the endoscope in FIG. 2 by the bending section.

Since the proximal-end joint group 12 in this embodiment has a bending angle of ±240°, there is a margin in the moving range after the tip 9 is turned through 180°; therefore, the tip 9 can be precisely translated. As shown in FIG. 12, the tip 9 can be translated along a straight path in the bending direction of the proximal-end joint group 12 by the cooperative motion of all bending joints 12a to 12d of the proximal-end joint group 12 and the bending joint 11c of the distal-end joint group 11.

As shown in FIGS. 13A and 13B, when the proximal-end joint group 12 is substantially straight, the tip 9 of the insertion part 7 can be advanced and retracted by bending the two peripheral bending joints 12a and 12d and the two central bending joints 12b and 12c of the four bending joints 12a to 12d in different directions such that the bending joints 12a to 12d move like an inchworm. This allows the position of the tip 9 to be finely adjusted without manually inserting the insertion part 7.

Figure 14A:
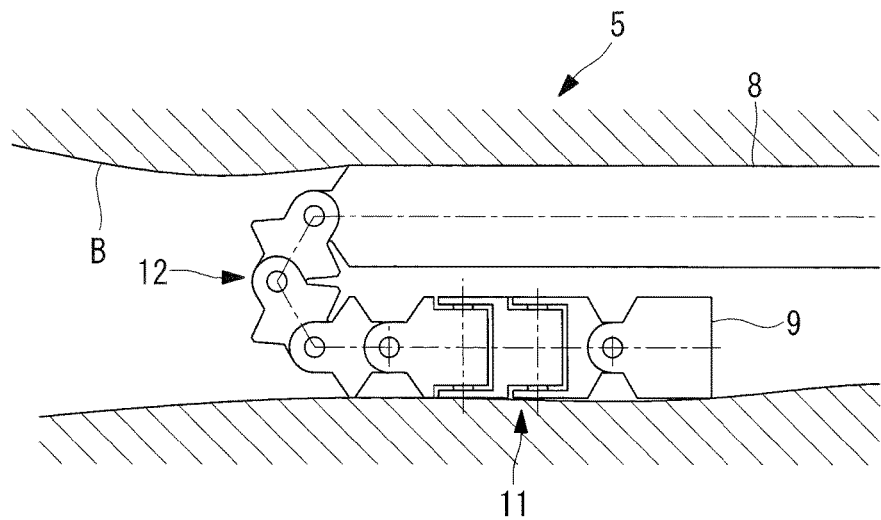
FIG. 14A is a side view showing the state where the bending section of the endoscope in FIG. 2 is inserted into a lumen.
Figure 14B:
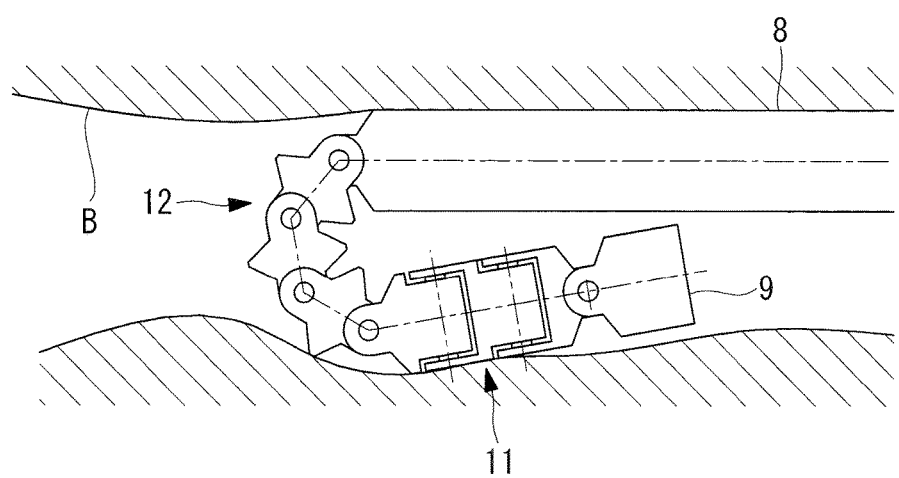
FIG. 14B is a side view showing the state where the bending section is fixed by the proximal-end joint group of the bending section.

As shown in FIGS. 14A and 14B, after the insertion part 7 is advanced through a lumen B to approach the affected area, the proximal-end joint group 12 may be bent into a U-shape, as shown in FIG. 14A, and the bent insertion part 7 may itself be pressed against the inner wall of the lumen B so as to expand the lumen B, as shown in FIG. 14B. This allows the insertion part 7 to be fixed relative to the lumen B and also ensures sufficient space for stable observation and treatment.

After the treatment is complete, the endoscope 5 can be removed from the lumen B by separating the drive units 6a and 6b from the drive sources 22 to allow all bending joints 11a to 11c and 12a to 12d to move passively and by manually removing the insertion part 7.

Figure 15A:
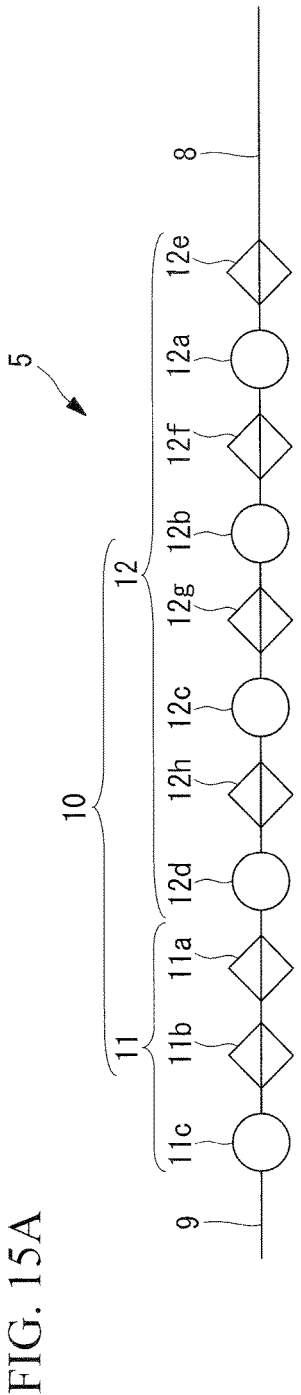
FIG. 15A is schematic side views showing first modification of the axial structure of the bending section of the endoscope in FIG. 2.
Figure 15B:
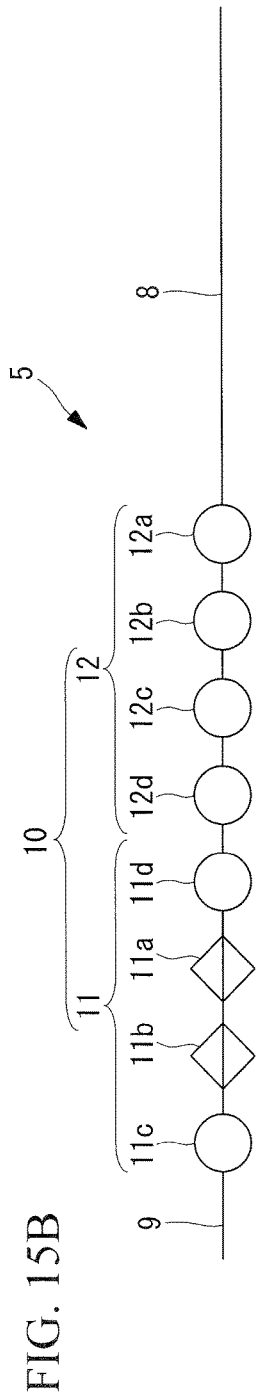
FIG. 15B is schematic side views showing second modification of the axial structure of the bending section of the endoscope in FIG. 2.

Although the bending section 10 illustrated in this embodiment includes the distal-end joint group 11, which is composed of the three bending joints 11a to 11c, and the proximal-end joint group 12, which is composed of the four bending joints 12a to 12d, this axial structure does not necessarily have to be used; other axial structures may be used, including those shown in FIGS. 15A and 15B.

FIG. 15A shows a proximal-end joint group 12 including four bending joints 12a to 12d having the axes thereof in the Y-axis direction and four bending joints 12e to 12h having the axes thereof in the Z-axis direction, rather than only the four bending joints 12a to 12d having the axes thereof in the Y-axis direction, and these bending joints are arranged alternately in the longitudinal axis direction. This allows the proximal-end joint group 12 to be bent through 180° or more in two axial directions.

FIG. 15B shows a distal-end joint group 11 including a bending joint 11d having the axis thereof in the Y-axis direction in addition to the three bending joints 11a to 11c. This allows the tip 9 to be translated while being maintained in the same orientation by the cooperative motion of the bending joints 11a to 11d that form the distal-end joint group 11.

Figure 15C:
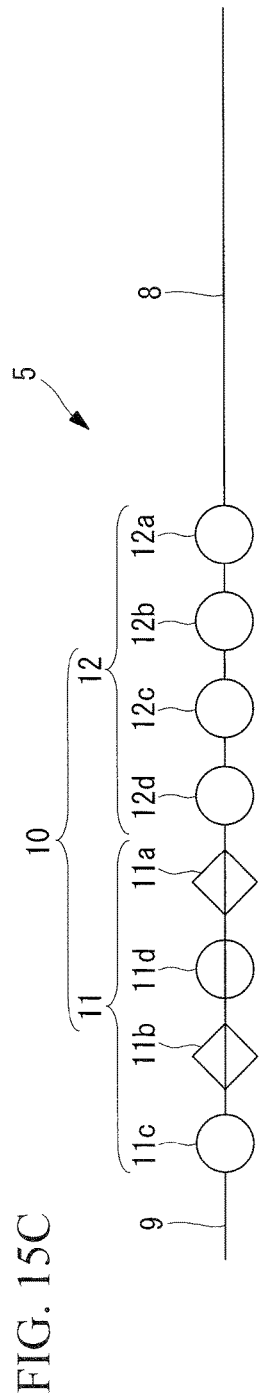
FIG. 15C is schematic side views showing third modification of the axial structure of the bending section of the endoscope in FIG. 2.

FIG. 15C shows a distal-end joint group 11 including four bending joints 11a to 11d, as does FIG. 15B; however, the bending joints 11c and 11d, which have the axes thereof in the Y-axis direction, and the bending joints 11a and 11b, which have the axes thereof in the Z-axis direction, are arranged alternately in the longitudinal axis direction. This distal-end joint group 11 can move in the same way as that in FIG. 15B.

Although the proximal-end joint group 12 illustrated in this embodiment has a total moving range of ±240°, it does not necessarily have to have such a moving range; it may have a moving range of 180° or more in at least one direction. This allows the tip 9 to be turned through 180°.

The proximal-end joint group 12 may include at least one bending joint in addition to a plurality of bending joints having a total moving range of 180° or more in at least one direction. This allows for a greater margin after the tip 9 is turned through 180°.

Although the joints illustrated in this embodiment are arranged at intervals with link members therebetween, the link members do not necessarily have to be used; the joints may be coupled together without link members therebetween. This allows for more bending.

Although the manipulator and manipulator system illustrated as an example in this embodiment are the endoscope 5 and the endoscope system 1, they do not necessarily have to be used for those applications; they may be used as a manipulator and a manipulator system for other applications, such as surgical instruments.

The above-described embodiment is derived from individual aspects of the present invention described below.

An aspect of the present invention provides a manipulator including a distal-end joint group and a proximal-end joint group that are arranged adjacent to each other in a distal-end section of an elongated insertion part in a longitudinal axis direction and that are configured to bend the distal-end section. The proximal-end joint group includes a plurality of proximal-end bending joints bendable about axes that are lined-up side-by-side to bend the distal-end section through 180° or more. The distal-end joint group includes a first distal-end bending joint disposed on a distal side of the proximal-end joint group and bendable about an axis crossing a plane including the axes of the proximal-end bending joints and the longitudinal axis; and a second distal-end bending joint disposed in the longitudinal axis direction relative to the axis of the first distal-end bending joint and bendable about an axis that is lined-up side-by-side with the axes of the proximal-end bending joints.

According to this aspect, the distal-end section can be substantially straightened by operating the distal-end joint group and the proximal-end joint group disposed at the distal end of the insertion part to improve the ease of insertion into an elongated straight lumen, and the bending joints that form the distal-end joint group and the proximal-end joint group can be appropriately bent about the axes thereof to allow smooth insertion into a curved lumen in conformity with the shape of the lumen.

For example, if an observation optical system is provided in the distal-end surface of the insertion part, it can be used to observe an affected area located in a field of view toward the front in the insertion direction. If the affected area cannot be observed in the field of view toward the front, for example, if the affected area is located behind a fold in the lumen, the distal-end section can be bent through 180° or more by operating the plurality of proximal-end bending joints that form the proximal-end joint group to direct the field of view toward the back in the insertion direction.

In this state, the distal end of the insertion part can be moved with two degrees of freedom by operating the first distal-end bending joint and the second distal-end bending joint provided in the distal-end joint group to observe and treat the affected area.

In the foregoing aspect, the proximal-end joint group may include one or more proximal-end bending joints in addition to the proximal-end bending joints configured to bend the distal-end section through 180° or more.

This allows the distal end of the insertion part to be moved by the one or more additional proximal-end bending joints when the distal end is directed toward the back in the insertion direction. The distal end can thus be translated in one direction by the cooperative motion of the one or more additional proximal-end bending joints and the second distal-end bending joint. This allows the distal end to be moved while being maintained in the same orientation and thus allows observation and treatment with reduced interference between the distal end and the inner wall of the lumen.

In the foregoing aspect, the proximal-end joint group may include three or more proximal-end bending joints.

This allows the distal-end section to be moved like an inchworm by the three or more proximal-end bending joints that form the proximal-end joint group so that the insertion part can be advanced and retracted in the longitudinal axis direction.

In the foregoing aspect, the distal-end joint group may include two or more first distal-end bending joints.

This allows the distal end of the insertion part to be translated in a direction crossing the moving direction of the second distal-end bending joint while being maintained in the same orientation.

In the foregoing aspect, the distal-end joint group may include two or more second distal-end bending joints.

This allows the distal end of the insertion part to be translated in a direction crossing the moving direction of the first distal-end bending joint without operating the proximal-end joint group.

Another aspect of the present invention provides a manipulator system including a slave device including any one of the foregoing manipulators and a drive unit configured to drive the manipulator; a master device including a manipulating part configured to be manipulated by an operator; and a controller configured to control the drive unit of the slave device based on an input signal input via the manipulating part of the master device.

REFERENCE SIGNS LIST

A doctor (operator)
1 endoscope system (manipulator system)
2 master device
3 slave device
4 controller
5 endoscope (manipulator)
6a distal-end drive unit (drive unit)
6b proximal-end drive unit (drive unit)
7 insertion part
9 tip
10 bending section (distal-end section)
11 distal-end joint group
11a, 11b bending joint (first distal-end bending joint)
11c bending joint (second distal-end bending joint)
12 proximal-end joint group
12a to 12h bending joint (proximal-end bending joint)

The invention claimed is:

1. A manipulator system comprising:
a slave device comprising:
an elongated insertion part extending along a longitudinal axis between a distal-end section and a proximal-end section;
a manipulator comprising:
a distal-end joint group and a proximal-end joint group arranged in the distal-end section, wherein the distal-end joint group and the proximal-end joint group are configured to be driven to bend the distal-end section,
wherein the proximal-end joint group comprises proximal-end bending joints configured to be bendable about axes that are lined-up side-by-side to bend the distal-end section through 180° or more, and
wherein the distal-end joint group comprises:
one or more first distal-end bending joints disposed more distally along the longitudinal axis than the proximal-end joint group, wherein the one or more first distal-end bending joints are configured to be bendable about an axis or axes perpendicular to a plane including the axes of the proximal-end bending joints and the longitudinal axis; and
a second distal-end bending joint disposed more distally along the longitudinal axis than the one or more first distal-end bending joints, wherein the second distal-end bending joint is configured to be bendable about an axis that is lined-up side-by-side with the axes of the proximal-end bending joints; and
a driver configured to be controlled to drive the manipulator;
a master device configured to receive an input by an operator and to output an input signal based on the input received; and
a controller configured to control, based on the input signal output by the master device, the driver to drive the proximal-end bending joints of the proximal-end joint group and the second distal-end bending joint of the distal-end joint group to bend in cooperative motion such that the distal-end section is translated along a straight path in a bending direction of the proximal-end joint group.

2. The manipulator system according to claim 1, wherein the proximal-end joint group comprises one or more proximal-end bending joints in addition to the proximal-end bending joints configured to bend the distal-end section through 180° or more.

3. The manipulator system according to claim 1, wherein the proximal-end joint group comprises three or more of the proximal-end bending joints.

4. The manipulator system according to claim 1, wherein the distal-end joint group comprises two or more of the first distal-end bending joint.

5. The manipulator system according to claim 1, wherein the distal-end joint group comprises two or more of the second distal-end bending joint.

6. A method for controlling a manipulator system comprising:
a slave device comprising:
an elongated insertion part extending along a longitudinal axis between a distal-end section and a proximal-end section;

a manipulator comprising:
  a distal-end joint group and a proximal-end joint group arranged in distal-end section, wherein the distal-end joint group and the proximal-end joint group are configured to be driven to bend the distal-end section,
  wherein the proximal-end joint group comprises proximal-end bending joints configured to be bendable about axes that are lined-up side-by-side to bend the distal-end section through 180° or more, and
  wherein the distal-end joint group comprises:
    one or more first distal-end bending joints disposed more distally along the longitudinal axis than the proximal-end joint group, wherein the one or more first distal-end bending joints are configured to be bendable about an axis or axes perpendicular to a plane including the axes of the proximal-end bending joints and the longitudinal axis; and
    a second distal-end bending joint disposed more distally along the longitudinal axis than the one or more first distal-end bending joints, wherein the second distal-end bending joint is configured to be bendable about an axis that is lined-up side-by-side with the axes of the proximal-end bending joints; and
  a driver configured to be controlled to drive the manipulator; and
a master device configured to receive an input by an operator and to output an input signal based on the input received,
wherein the method comprises:
  controlling, based on the input signal output by the master device, the driver to drive the proximal-end bending joints of the proximal-end joint group and the second distal-end bending joint of the distal-end joint group to bend in cooperative motion such that the distal-end section is translated along a straight path in a bending direction of the proximal-end joint group.

* * * * *